(12) United States Patent
Lemanski

(10) Patent No.: US 10,653,121 B2
(45) Date of Patent: May 19, 2020

(54) DECORATIVE ANT FARM

(71) Applicant: Jacob Samuel Lemanski, Boulder, CO (US)

(72) Inventor: Jacob Samuel Lemanski, Boulder, CO (US)

(*) Notice: Subject to any disclaimer, the term of this patent is extended or adjusted under 35 U.S.C. 154(b) by 0 days.

(21) Appl. No.: 16/045,579

(22) Filed: Jul. 25, 2018

(65) Prior Publication Data
US 2020/0029537 A1 Jan. 30, 2020

(51) Int. Cl.
A01K 63/00 (2017.01)
A01K 67/033 (2006.01)
F21V 33/00 (2006.01)
F21W 121/00 (2006.01)
F21Y 115/10 (2016.01)

(52) U.S. Cl.
CPC .......... A01K 63/006 (2013.01); A01K 67/033 (2013.01); F21V 33/008 (2013.01); F21W 2121/00 (2013.01); F21Y 2115/10 (2016.08)

(58) Field of Classification Search
CPC .................................................. A01K 63/006
See application file for complete search history.

(56) References Cited

U.S. PATENT DOCUMENTS

| 3,119,371 | A | * | 1/1964 | Zuckerman | A01K 63/006 119/258 |
| 6,742,477 | B1 | * | 6/2004 | Marraudino | A01K 63/006 119/256 |
| 10,285,386 | B2 | * | 5/2019 | Zinno | A01K 63/06 |
| 2006/0082023 | A1 | * | 4/2006 | Hones | B44C 5/005 264/299 |
| 2006/0238996 | A1 | * | 10/2006 | Hones | A01K 63/006 362/127 |
| 2007/0234967 | A1 | * | 10/2007 | Margerum | A01K 63/003 119/257 |
| 2009/0147502 | A1 | * | 6/2009 | Aleman | A01K 63/006 362/101 |
| 2011/0048332 | A1 | * | 3/2011 | Lee | A01K 63/06 119/253 |

FOREIGN PATENT DOCUMENTS

CN 107667950 A * 2/2018

OTHER PUBLICATIONS

English Translation of CN107667950A (Year: 2018).*
Fascinations AntWorks Illuminated Blue, Amazon.com (Year: 2014).*

* cited by examiner

Primary Examiner — Charlie Y Peng
(74) Attorney, Agent, or Firm — Will Hunziker

(57) ABSTRACT

An ant farm with an internal light source to front or backlight a decorative background image within a frame to maximize the easthetic beauty of the ant farm.

9 Claims, 2 Drawing Sheets

DECORATIVE ANT FARM

BACKGROUND OF THE INVENTION

1. Field of the Invention

The present invention is in the technical field of ant farms.

2. Description of Related Art

A formicarium, or ant farm, is a vivarium that is designed primarily for the study of ant colonies and how ants behave. The formicarium reduces the three dimensions of an ants' nest to the virtual two dimensions between two planes of glass. The ant farm was first displayed at the Exposition Universelle at Paris in 1900 and went into commercial production around 1929. Previous versions of ant farms occasionally had painted backgrounds above the ground level of the formicarium. No prior versions of formicariums have built in light sources that light up a decorative background image to make the ant farm more visually appealing.

SUMMARY

The scope of the present invention is defined solely by the appended claims and detailed description of a preferred embodiment, and is not affected to any degree by the statements within this summary. The ant farm described herein may have integrated lighting to front or backlight a decorative background image within a sealed frame to maximize the easthetic beauty of the ant farm. Such light source may be arranged around the interior circumference of the frame and be shielded by the frame from letting light out from any direction other than the front of the frame. Additional features are also described.

BRIEF DESCRIPTION OF THE DRAWINGS

Various embodiments are described herein with reference to the following Drawings Certain aspects of the Drawings are depicted in a simplified way for reason of clarity. Not all alternatives and options are shown in the Drawings and, therefore, the Claims are not limited in scope to the content of the Drawings.

1. FIGURES

Figure 1:
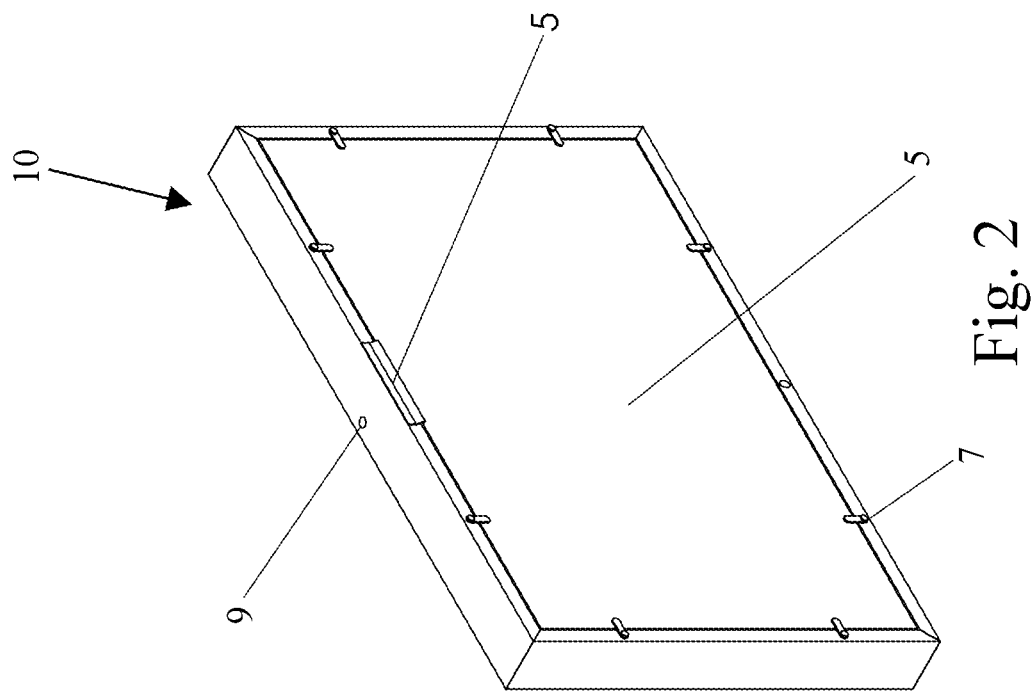

FIG. 1 illustrates a front perspective view of an ant farm, in accordance with an embodiment of the present disclosure.

Figure 2:
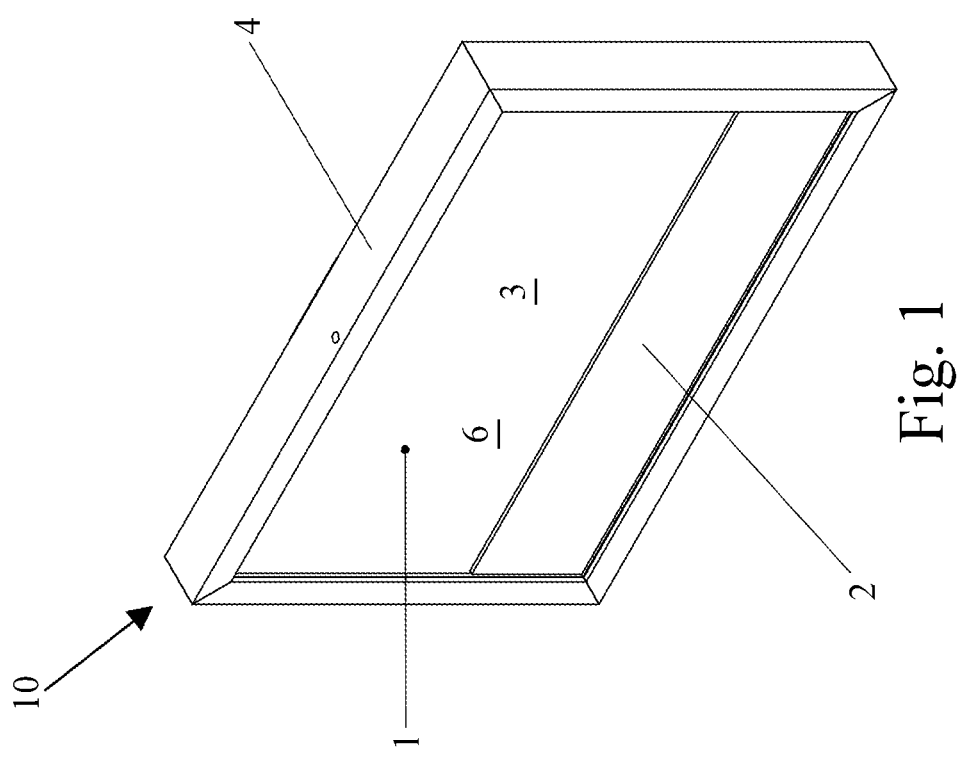

FIG. 2 illustrates a rear perspective view of an ant farm, in accordance with an embodiment of the present disclosure.

Figure 3:
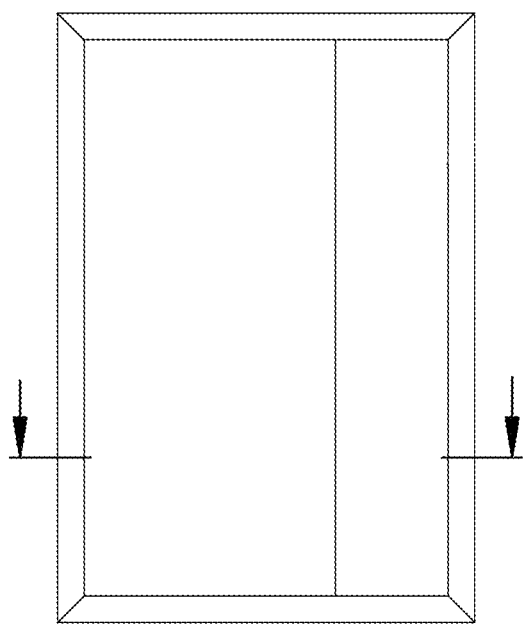

FIG. 3 illustrates a front view of an ant farm, in accordance with an embodiment of the present disclosure.

Figure 4:
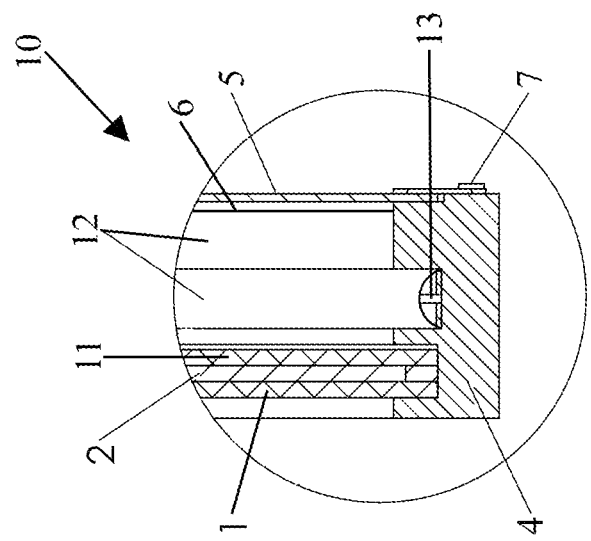
Figure 4:

FIG. 4 illustrates a cutaway view of FIG. 3, in accordance with an embodiment of the present disclosure.

FIG. 5 illustrates a magnified view of a detail of FIG. 4, in accordance with an embodiment of the present disclosure.

Corresponding reference characters indicate corresponding components throughout the several figures of the Drawings. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiment are often not depicted in order to facilitate a less obstructed view of these various embodiments of the present disclosure.

2. REFERENCES

1 Translucent Exterior Front Panel
2 Digging Or Planting Medium
3 Space Above The Digging Or Planting Medium
4 Frame
5 Exterior Rear Panel
6 Background Image
7 Rear Exterior Panel Attachment
8 Wall Attachment
9 Access To The Interior Of The Ant Farm
10 Ant Farm
11 Interior Translucent Front Panel
12 Interior Air Space
13 Light Source(s)

DETAILED DESCRIPTION

The following description is not to be taken in a limiting sense, but is made merely for the purpose of describing the general principles of exemplary embodiments, many additional embodiments of this invention are possible. It is understood that no limitation of the scope of the invention is thereby intended. The scope of the disclosure should be determined with reference to the Claims. Reference throughout this specification to "one embodiment," "an embodiment," or similar language means that a particular feature, structure, or characteristic that is described in connection with the embodiment is included in at least one embodiment of the present disclosure. Thus, appearances of the phrases "in one embodiment," "in an embodiment," and similar language throughout this specification may, but do not necessarily, all refer to the same embodiment.

Further, the described features, structures, or characteristics of the present disclosure may be combined in any suitable manner in one or more embodiments. In the Detailed Description, numerous specific details are provided for a thorough understanding of embodiments of the disclosure. One skilled in the relevant art will recognize, however, that the embodiments of the present disclosure can be practiced without one or more of the specific details, or with other methods, components, materials, and so forth. In other instances, well-known structures, materials, or operations are not shown or described in detail to avoid obscuring aspects of the present disclosure.

Unless otherwise indicated, the drawings are intended to be read (e.g., arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "internal" and "external" generally refer to the orientation of a wall relative the interior or exterior of the ant farm. Also, as used herein, terms such as "positioned on" or "supported on" mean positioned or supported on but not necessarily in direct contact with the wall.

For the purposes of promoting an understanding of the principles of the present invention, reference will now be made to the embodiments illustrated in the drawings and specific language will be used to describe the same. Generally, the invention comprises an ant farm. The term "ant farm" as used in this detailed description and in the claims below describes an enclosed area used for the observation of plants, animals, or insects, a "vivarium" in the form of a container with at least one transparent side for the viewing of the incased plants, animals, or insects. Essentially, an ant farm is not required to have ants. An ant farm can be made of any material suitable to its purpose, such as glass, plastic, metal, wood, ceramic, etc. An ant farm may also be free standing or require attachment to a wall or other wall. An ant farm may also be fully enclosed or lidless.

FIG. 1 shows a front perspective view of an embodiment of an ant farm (10). In this embodiment the ant farm (10) comprises at least one translucent exterior front panels (1) that allows the user to observe the inside of the ant farm, such translucent exterior panels (1) typically being on the front of the ant farm (10). Said at least one translucent exterior panel (1) is typically made from glass, acrylic, or plastic; but could be of another translucent material. The ant farm (10) also comprises a digging or planting medium (2) such as sand, colored sand, dirt, soil, clay, etc that plants, animals, or insects can live in or upon. This digging or planting medium (2) typically fills about half to two thirds of the height of the space in the container available for it, leaving a space above the digging or planting medium (3). This embodiment of an ant farm (10) has a frame (4) that surrounds at least the left and right sides as well as the bottom of the ant farm and may or may not surround the top of the ant farm. The frame may be translucent or opaque.

Now looking at FIG. 2, which illustrates a rear perspective view of the same embodiment of an ant farm as shown in FIG. 1 we can see the ant farm (10) also comprises one or more exterior rear panels (5). Said exterior rear panel (5) may have a background image (6) on it's interior surface, or said background image can placed at another location inside the ant farm (10) from which can be seen through the one or more translucent exterior front panels (1) where such background image (6) is not obscured by said digging or planting medium (3) as seen in FIG. 1. Said background image may also be produced by a television screen which may also act as a source of light. Said rear panel (5) may have attachments (7) to said ant farm (10) by a variety methods: for example; it could be permanently affixed, or removably affixed with glue, staples, screws, turn buttons (as shown), clips, pressure fitted, slides, snaps, ties, buttons, or etc. The ant farm frame (4) may be placed upright on a wall or hung on a wall with a wall attachment (8), such as a wire or possibly by a cleat on the back of the frame allowing it to be mounted on a wall. If the ant farm frame does not have an open top, then the ant farm (10) must also have an access the interior of the ant farm (9), as illustrated that can be a button to remove a lid, it could be a hole or long slot, a lid could simply be placed on it and gravity could hold it down, it could be pressure fitted, snapped, clipped, tied, twisted, screwed, snapped, etc. The access to the ant farm (9) allows access to the interior habitat for feeding and watering.

The rest of the functional elements of the embodiment of an ant farm shown in FIGS. 1 and 2 are internal to the ant farm; as such, proper orientation is needed to describe such elements. FIG. 3 is the same embodiment of an ant farm as shown in FIGS. 1 and 2 wherein a slice perpendicular to its length is labeled (A). If FIG. 3 is seen as a cut away view from the perspective of A then the viewer sees Fig. A. There is a small circle at the base of Fig. A labeled (B); if the details of that small circle are magnified then you see what is shown in Fig. B.

Now addressing what is shown in Fig. B. Fig. B shows the visible elements of the embodiment of the ant farm shown in FIGS. 1 and 2; comprising: one or more translucent exterior front panels (1), digging or planting medium (2), a frame (4), a rear panel (5), a background image (6), and a rear panel attachment (7). Fig. B also shows additional internal elements, which may comprise: one or more interior translucent front panels (11), and one or more air spaces (12). Importantly, Fig. B shows one or more light source(s) (13). Said light sources can be LEDs (as shown), bulbs, light strips, florescence, etc. Said light source(s) may be all around the periphery of the interior of the frame (4). Said light source(s) (13) may be projected into the interior of the ant farm (10) between the one or more exterior translucent front panels of the ant farm (1) and the rear panel (5); wherein the light source(s) (13) illuminate said background image through the one or more exterior (1) and/or interior translucent front panels (11) for a viewer to see. Said background image (6) can be either be behind the light source (as pictured) or in front of the light source so long as the background image is also translucent so that the light source (13) can backlight the background image through the interior and exterior translucent front panels for a viewer.

It is important that the light source is interior to the ant farms as ant farms have already had backgrounds painted behind the exterior translucent wall before. This invention is primarily about an ant farm that has its own source of light to light a background image that is viewable through the front of the ant farm. This lighting is particularly effective when the light is projected into an airspace (12) in front of a background image (6), giving the back ground image some space behind the behind the digging or planting medium (2) to give the background image the perspective of distance. It is also most effective when the one or more exterior rear panels and the frame of the ant farm are not translucent, thereby creating a glowing effect which emanates only from the front of the ant farm, thereby illuminating its contents for easy viewing.

The function of an ant farm is typically to add seeds and digging insects such as ants or termites to the habitat. Importantly, the habitat wherein the plants, animals, or insects live is thin (possibly as thin as 0.25 inches) such that the tunnels created by the insects are clear through to the background image (6). The thinness of the ant farm also makes the root systems of plants easy to see, especially when backlit. Controlling the color of the lights also changes the apparent color of the background image. Optionally, the background image may be interchangeable, or could even be produced by an audio visual screen such as an LED, plasma, OLED, tube or other type of television or projector. The habitat may also be removed from the frame then disassembled for cleaning. The lights may also be controlled over Wi-Fi using an app or as a separate option they can be wired directly to an input such as analog knobs.

Larger ant farms (10) may typically go together differently than smaller ones, the main difference being that the smaller ones usually have a lid that comes off the top to remove the habitat and the larger ones have a external and internal translucent front panels that sandwich the habitat.

Information as herein shown and described in detail is fully capable of attaining the above-described object of the present disclosure, the presently preferred embodiment of the present disclosure; and is, thus, representative of the subject matter; which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above described preferred embodiment and additional embodiments as regarded by those of ordinary skill in the art are hereby expressly incorporated by reference and are intended to be encompassed by the present claims.

What is claimed is:

1. An ant farm, comprising:
   a frame with a bottom, two sides, and an interior;
   a translucent exterior front wall;
   a digging or planting medium;
   a translucent interior front wall, wherein the distance between said exterior and said interior front wall is thin enough to allow tunnels created by insects to be clear to see through;
   an interior light source, wherein said light source is embedded in the frame and surround the periphery of the frame;
   a background image;
   an exterior rear panel, and
   wherein said interior light source illuminates an open-air space between said translucent interior front wall and the background image, thereby giving the background image the perspective of distance when view through the tunnels.

2. The ant farm of claim 1, wherein said interior light source is an LED light.

3. The ant farm of claim 1, wherein said exterior rear panel and said frame are not translucent.

4. The ant farm of claim 1, wherein said background image is produced by a television screen.

5. The ant farm of claim 1, wherein said exterior rear panel and said frame are not translucent.

6. The ant farm of claim 1, wherein said distance between said exterior front wall and said interior front wall is 0.25 inches.

7. The ant farm of claim 1, wherein said interior and exterior front panels form a removable habitat with said digging medium contained within.

8. The ant farm of claim 7, wherein the habitat may also be removed from the frame then disassembled for cleaning.

9. The ant farm of claim 1, wherein said light source may be controlled with a remote control, over Wi-Fi using an app, or with analog knobs.

* * * * *